United States Patent [19]
Markham et al.

[11] Patent Number: 5,242,471
[45] Date of Patent: Sep. 7, 1993

[54] COUPLING CAPILLARY GAS CHROMATOGRAPHY TO TRADITIONAL LIQUID CHROMATOGRAPHY DETECTORS

[75] Inventors: Dan A. Markham, Rhodes; Patrick W. Langvardt, Midland, both of Mich.

[73] Assignee: The Dow Chemical Company, Midland, Mich.

[21] Appl. No.: 887,996

[22] Filed: May 22, 1992

[51] Int. Cl.$^5$ .............................. B01D 15/08
[52] U.S. Cl. ...................... 95/87; 73/23.37; 73/23.4; 96/105
[58] Field of Search ............... 55/67, 197, 208, 386; 73/23.35, 23.37, 23.4, 61.58

[56] References Cited

U.S. PATENT DOCUMENTS

| | | | |
|---|---|---|---|
| 4,684,470 | 8/1987 | Peters et al. | 210/639 |
| 4,814,089 | 3/1989 | Kumar | 55/67 X |
| 4,917,709 | 4/1990 | Hall et al. | 55/67 X |

OTHER PUBLICATIONS

Skoog et al., *Principles of Instrumental Analysis*, (2nd Ed.), 1980, Table of Contents.

Primary Examiner—Robert Spitzer
Attorney, Agent, or Firm—James T. Hoppe; Burke M. Hallderson

[57] ABSTRACT

Apparatus and methods are provided for using a detector designed for use with liquids to detect resolved analytes in an effluent stream from a gas chromatography instrument. The gaseous stream is entrained by a flowing liquid solvent, and at least a portion of the analytes are transferred from the gas phase to the liquid phase. The liquid solvent containing the analytes is then conveyed to a detector designed for liquid analysis. Thus, the present invention gives the analyst more options for detecting an analyte or a group of analytes, thereby providing greater flexibility in optimizing the sensitivity or selectivity of the analysis. Furthermore, the present invention allows gaseous effluents to be analyzed by detectors which more readily permit sample recovery than the detectors currently being used to analyze gaseous effluents.

21 Claims, 5 Drawing Sheets

COUPLING CAPILLARY GAS CHROMATOGRAPHY TO TRADITIONAL LIQUID CHROMATOGRAPHY DETECTORS

BACKGROUND OF THE INVENTION

The present invention pertains to gas chromatography and more particularly to an on-line system and method which allows the analytes eluting from a chromatography column to be analyzed by traditional liquid detectors. Still more particularly, this invention relates to coupling a capillary gas chromatograph to a liquid radioactivity monitor.

There are several known techniques to separate a sample of a mixture into its various components. Separation techniques based on selective retention make up the general field of chromatography. Generally, separation in chromatography is due to redistribution of the molecules of a mixture between a mobile phase and a stationary phase which is held in a column. Gas chromatography is the branch of chromatography which uses a gas as the mobile phase. In gas chromatography the sample must be in vapor form in order for the gaseous mobile phase to carry the sample to the column. The components of the sample are then separated according to the rate at which the molecules of each component exchange with the stationary phase. Those components with the least affinity towards the stationary phase will elute from the column first.

The effluent from the column is continually monitored in order to detect when a component elutes from the column. Several types of detection systems are currently being used for gas chromatography. One type of detection system which is particularly useful when the sample contains isotopes which emit ionizing radiation, is a radiogas detector.

Radiogas detectors typically involve a catalytic combustion of a radiolabeled sample to form $^{14}CO_2$ gas. This gas is then brought into contact with a scintillator matrix which is capable of converting radioactive energy into light. A detector is then used to count the number of light pulses over a period of time. The number of counts per unit of time changes in response to the presence of radiolabeled compounds which have been separated out by the gas chromatograph. Thus, as the analysis begins, the number of counts per minute is low representing only background radiation. Then when the first compound which emits ionizing radiation elutes from the column, the number of counts per minute quickly increases indicating the presence of the radiation. After the compound has completely eluted from the column and traveled past the counter, the number of counts per minute decreases back to the background level. This process continues until every compound separated by the capillary gas chromatography column has eluted from the column.

Radiogas detection systems have some significant drawbacks, however. First, radiogas detectors suffer from recovery loss as the catalytic combustion process is not 100% efficient. Furthermore, the efficiency of the combustion process changes over time as components of the combustion tube are depleted and/or contaminated. Accordingly, it is not possible to determine quantitative system recoveries. Secondly, because radiogas detectors use counting tubes having relatively large volumes to count the pulses of light, they are not capable of simultaneously providing high chromatographic resolution with high sensitivity. Resolution and sensitivity are directly related to the size of the counting tube in the detector. The larger the tube, the greater the sensitivity, but the less the resolution due to the diffusion of the gaseous molecules. Similarly, when the size of the counting tube is reduced in order to achieve better resolution, the sensitivity is decreased due to less scintillating material being present.

Both of these drawbacks could be improved if a liquid radioactivity monitor rather than a radiogas monitor could be used. Liquid radioactivity monitors (LRAM) are based on the same principle as radiogas monitors, but operate in the liquid rather than gaseous phase. Thus, the concentration of scintillating material can be increased, because the solubility of the scintillating material is much greater in a liquid phase than in a gaseous phase. Furthermore, diffusion rates are much slower in liquid phases than in gas phases, so liquid radiogas monitors maintain peak resolution better than the radiogas detectors. Accordingly, it would be advantageous to combine the separation powers of gas chromatography with the sensitivity and peak resolution of a liquid radioactivity detector. Malcolm Bowman and Morton Beroza, in *Analytical Chemistry, Vol.40. No.3*, pg 535, Mar. 1968, have reported using a packed column GC coupled to a spectrophotofluorometer via an open flowing interface. Their interface coupled the effluent from a GC to a mixing vessel which had a stream of solvent flowing through it, and an open tube which allowed the carrier gas to escape. Their interface also permits the more volatile analytes to escape with the carrier gas, however, preventing their detection. Furthermore, the resolution achieved is poor (e.g. a 0.2 $\mu$g sample of fluorene, at an oven temperature of 150° C. resulted in a peak which took over 2 minutes to completely elute). Thus, Bowman and Beroza's interface is not adequate for many applications.

It would be beneficial to combine a chromatography instrument with "real-time" liquid radioactivity monitoring via a closed transfer interface, so that sensitivity and resolution can be maintained. Such a combination is a primary objective of the present invention.

It is another objective of the present invention to provide an improved method for analyzing a sample containing particles which emit ionizing radiation.

It is a further objective of the present invention to provide an interface facilitating the coupling of gas chromatographic instruments to any detector designed for liquid streams.

Still another objective of the present invention is to provide a system which allows analytes in a gaseous stream to be continually derivatized facilitating detection.

SUMMARY OF THE INVENTION

To achieve the forgoing objectives, the present invention provides a chromatographic method and apparatus for analyzing a gaseous sample. The system includes a chromatographic instrument, an interface designed to entrain the gaseous effluent from the chromatograph with a liquid solvent, a pump for delivering the liquid solvent containing the scintillating material, and a detector typically used to analyze liquids.

In accordance with the method of the present invention, a sample is separated into its various components by preferably capillary gas chromatography. The effluent from the gas chromatography column is transported to an entrainment zone via a transfer line. This transfer line is preferably heated in order to maintain the separation achieved by the gas chromatography column. Meanwhile a stream of solvent is also continually pumped into the entrainment zone, such that the GC effluent becomes entrained within the stream of solvent. The resulting stream of liquid containing the entrained gas then travels out of the entrainment zone towards a detector. As the stream of liquid containing the entrained gas travels towards the detector, at least a portion of the analytes are transferred from the gaseous effluent to the liquid solvent, thereby allowing a detector designed for analyzing liquids to be used to monitor the analytes.

The apparatus and method can be used to analyze samples labelled with particles which emit ionizing radiation. To accomplish this the liquid solvent is mixed with a scintillating material before being pumped into the entrainment zone. Furthermore, the detector chosen in this circumstance should be a liquid radioactivity monitor.

Accordingly, it should be appreciated that the system and method of the present invention allows the gaseous effluent of a chromatographic instrument to be analyzed by detectors used in liquid analysis. Thus, the present invention gives the analyst more options for detecting an analyte or a group of analytes, thereby providing greater flexibility in optimizing the sensitivity or selectivity of the analysis. Furthermore, the present invention allows gaseous effluents to be analyzed by detectors which more readily permit sample recovery than the detectors currently being used to analyze gaseous effluents.

Additional advantages and features of the present invention will become apparent from reading of the detailed description of a preferred embodiment which makes reference to the following set of drawings in which:

DETAILED DESCRIPTION OF THE INVENTION

It should be understood that specific details of the invention described below, such as materials, dimensions, and commercial part designations, are not to be considered limitations in the invention. Rather, these details should be considered as merely representing a preferred embodiment of the invention.

Figure 1:
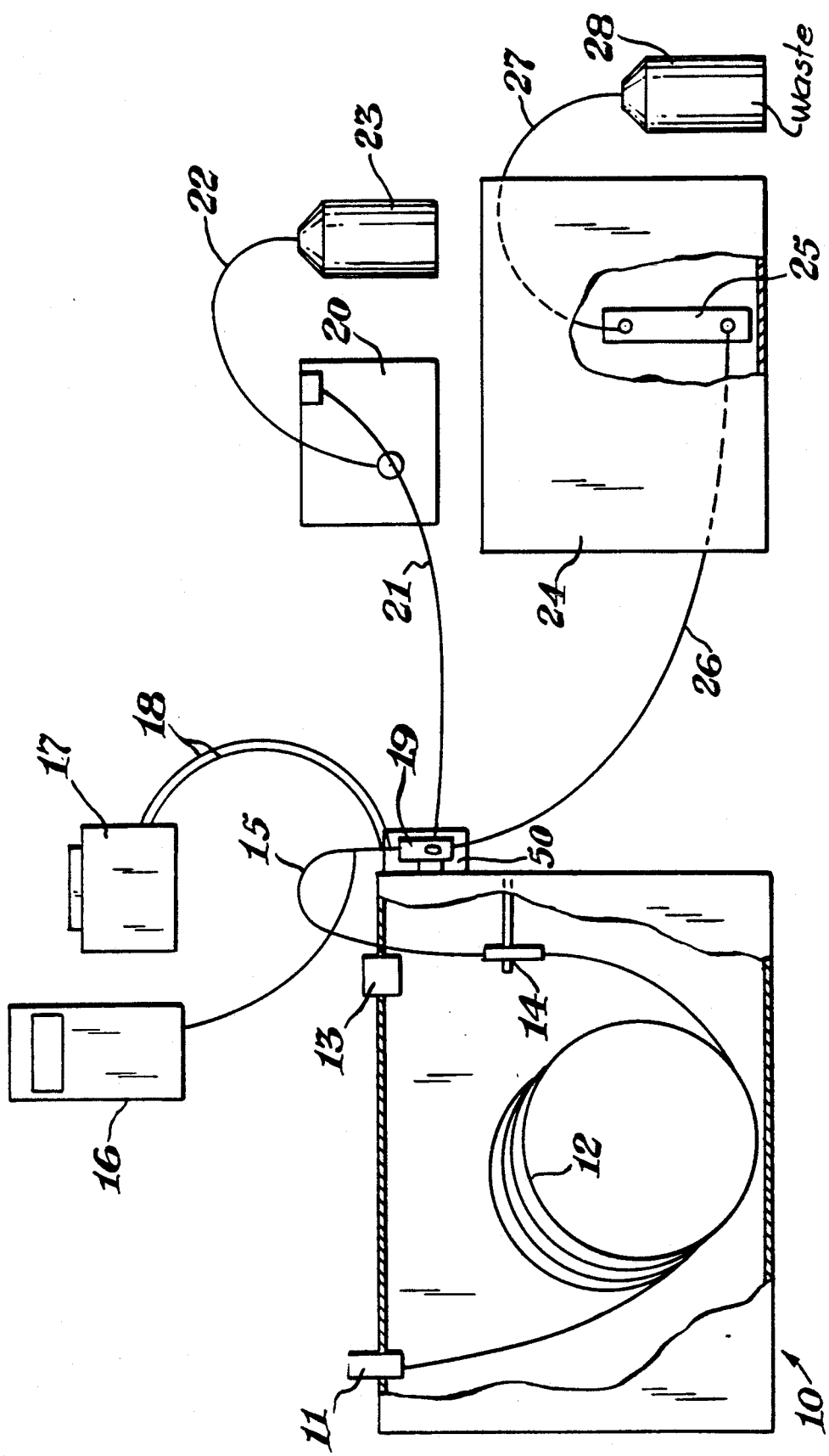
FIG. 1 is a side elevational view with parts broken away to illustrate internal detail of a gas chromatography-liquid radioactivity monitor detection system which illustrates a preferred embodiment of an apparatus constructed according to the principles of the present invention.

As seen in FIG. 1, the chromatographic system of the present invention includes a typical gas chromatography column 12 which receives a sample to be analyzed from an injector 11. As an example of a suitable set of chromatographic conditions, the injector 11 may be comprised of a Restek direct injection liner, part no. 20309, and operated at typical flash-injection temperatures. The column 12 may be comprised of a fused silica capillary column such as J & W DB-624 30w 1.8 82 m. In one application the temperature of the oven 10 containing the column 12 is kept at 40° C. for 5 minutes after the sample has been injected, then is raised at the rate of 15° C./min to a temperature of 175° C., and then held steady for an additional minute. Many other temperature gradients, and instrument variations which are known to be effective for separating various components can also be used with this invention. Additionally, the carrier gas should be at a high enough pressure to overcome any back pressure developed from the entrainment zone 19. Helium at 20 psi has been shown to be effective for accomplishing the goals of the above application.

Figure 2:
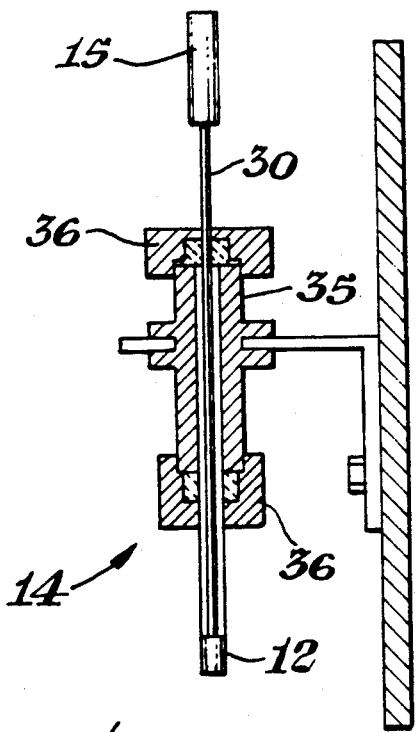
FIG. 2 is a cross-sectional view of a suitable junction for joining the output of a capillary column to an interface suitable for use with this invention.

As seen in FIG. 2, the outlet end of the gas chromatography column 12 is connected to a transfer line 30 at junction 14. The transfer line 30 allows the gaseous effluent to be conveyed from the GC column 12 to the entrainment zone 19. The junction 14, should be designed so that dead volume is kept at a minimum, as increased dead volume causes a reduction in the separation achieved by the chromatography column due to the high diffusion rates in gaseous phases. One suitable junction for use with the invention is pictured in FIG. 2. That drawing depicts the capillary column 12 entering a stainless steel bulkhead 35 with Swagelok fittings. At the other end of the bulkhead 35, a 300 $\mu$m o.d. $\times$ 200 $\mu$m i.d. the deactivated fused silica capillary tubing 30 which makes up part of the transfer line 15 is shown. The capillary column 12 and the deactivated fused silica capillary tubing 30 are sealed at the bulkhead 35 with 0.4 mm 60% vespel/40% graphite ferrules 36.

Figure 3:
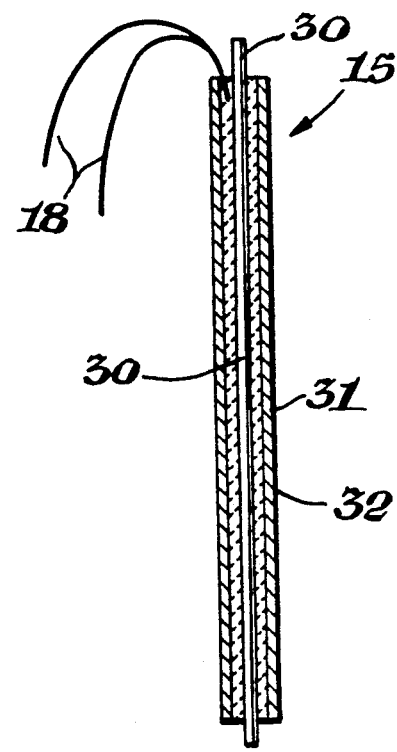
FIG. 3 is a cross-sectional view of a heated transfer line which can be used to convey the gaseous effluent to an entrainment zone.

As best seen in FIG. 3, the transfer line 30, which can be constructed from deactivated fused silica capillary tubing, is preferably jacketed by a 1/16 inch stainless steel tubing 31. The area between the outside of the transfer line 30 and the inside of the stainless steel tubing 31, is preferably filled with an insulating material 32. Heating leads 18 allow the transfer line 30 to be maintained at a high temperature, typically between 150° C. and 250° C. Heating the transfer line 30 helps to keep the bands of analytes which have been separated in the GC column from reuniting before they reach the entrainment zone 19. The transfer line 30, the stainless steel tubing 31, the insulating material 32, and the heating leads 18 are collectively referred to as the heated transfer line 15.

Returning to FIG. 1, the heating leads 18 of the heated transfer line 15 are shown attached to a rheostat 17. Furthermore, a thermocouple 16 is provided to measure the temperature of the deactivated fused silica capillary tubing 30 within the heated transfer line 15. Thus, the rheostat 17 can be adjusted as needed to maintain the desired temperature of the heated transfer line 15.

Alternatively, the entrainment zone 19 could be located within the gas chromatography instrument, eliminating the need for the heated transfer line 15, rheostat 17 and thermocouple 16. This is not preferred, however, as it is often desirable to use highly flammable materials as the solvent. Thus, placing the entrainment zone 19 inside the GC oven 10 potentially poses a serious safety hazard.

Figure 4:
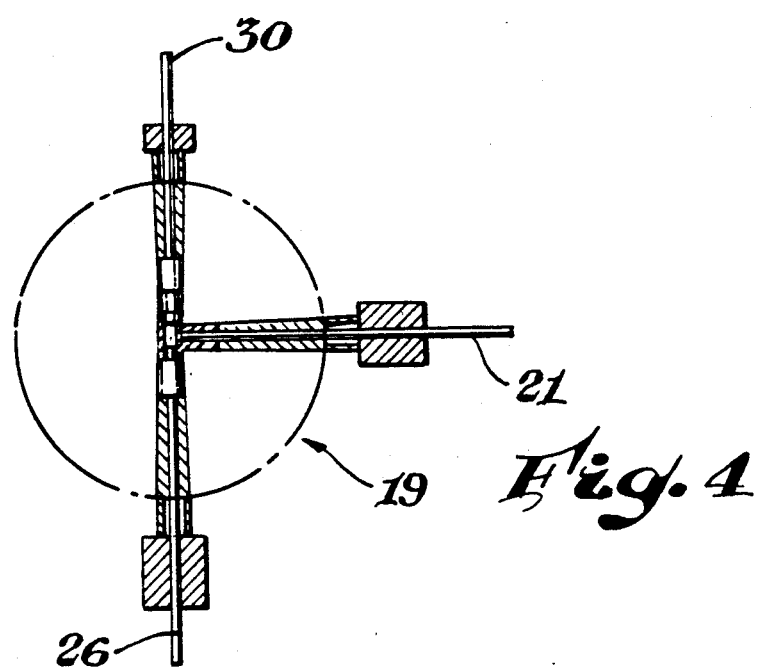
FIG. 4 is a side-elevational view partially in section of an entrainment zone suitable for entraining the gaseous effluent in a liquid solvent.

FIG. 4 depicts an entrainment zone 19 suitable for use with this invention. The zone is preferably comprised of a tee, such as those manufactured by Valco (part no. ZT1C). The tee should be constructed to minimize dead volume, preferably eliminating dead volume altogether (a zero-dead volume tee). The 1/16 inch stainless steel tubing 31 (not shown in FIG. 4), and the deactivated fused silica capillary tubing 30 of the heated transfer line 15 are sealed at one arm of the tee, e. g. with a Valco fused silica adapter (part no. FS1-4). The deactivated fused silica capillary tubing 30 is positioned in the tee such that the end of the tubing 30 extends past the ferrule approximately 1 mm.

A second arm of the tee admits a liquid solvent to the entrainment zone 19. The solvent entrains the gas containing the analytes from the deactivated fused silica capillary tubing 30 forming a gas/liquid stream. "Entrain" for this invention means that the gaseous effluent from the gas chromatograph is carried along by the flowing solvent. Thus, as some finite amount of the gas enters the entrainment zone 19 it is immediately surrounded by fluid, forming a gas bubble. Preferably, this gas bubble is in the form of segments, such that the flow through tubing 26 alternates between segments of the liquid phase and segments of the gaseous phase. For a better understanding of segmented flow and its benefits see U.S. Pat. No. 4,684,470 to Peters et al., which is hereby incorporated by reference.

The configuration of the tee shown in FIG. 4, with the gaseous effluent coming in one side of the tee, the liquid solvent flowing in from the base of the tee, and the combined liquid-gas stream flowing out of the other side of the tee, is preferred. This configuration has been shown to be the most effective at entraining the gaseous effluent while generally maintaining the resolution achieved by the gas chromatograph.

The resulting stream of solvent and entrained gas flows out of the entrainment zone 19 via tubing 26 and to the detector 24. As the stream flows through tubing 26, the analytes are transferred from the gas phase to the liquid phase, allowing them to be detected by the detector 24. Accordingly, a solvent in which the anticipated analytes are readily soluble should be selected. The solvent should also be inert towards the analytes. There are many possible choices of solvent for carrying out the method of the present invention. Furthermore, the solvent can be a combination of liquids so that certain desired attributes are maximized, such as increasing the solubility of the solvent for a wider range of analytes. In a preferred embodiment of the present invention, the reservoir 23 contains acetonitrile as the solvent.

The solvent is pumped into the entrainment zone 19 via tubing 21, and the resulting stream of solvent and entrained gas is conveyed to the detector 24 via tubing 26. Tubing 21 and 26 may be constructed from 0.01 inch i.d. stainless steel tubing which can be sealed at the tee using the appropriate stainless steel nuts and ferrules. The entrainment zone 19 is preferably heated to facilitate efficient transfers of material. Towards this end, the entrainment zone 19 is shown housed in a machined aluminum-block 50 and heat is supplied by a cartridge heater which is controlled using a thermocouple and a heated zone of the GC. The junction 14, heated transfer line 15, low volume tee 19, entrainment zone heating block 50 and the connecting tubing 21, and 26, are collectively referred to as the interface of this invention.

Returning to FIG. 1, a pump 20 is shown in fluid connection via tubing 22 with a reservoir 23 of solvent. The pump can be any number of commercially available pumps, so long as it can deliver the solvent at a controlled rate (typically on the order of 3 ml/min), and is inert towards the solvent. One example of a suitable pump is Waters model no. M-45. The rate of pumping should be optimized for each analysis. A faster rate of pumping improves the apparent chromatographic efficiency (provides narrower peaks), but decreases sensitivity, as there will be less residence time in the liquid detector cell. Thus, an analyst can adjust the flow of the solvent according to the needs of a particular analysis.

As an alternative to using a pump to deliver the solvent to the entrainment zone, a gravity driven system could be assembled to deliver a stream of solvent to the tee 19. Such a system is not preferred, however, because relatively large pressures must be maintained in order to overcome the pressures used in the GC. If the pressure is insufficient, the effluent from the GC will travel upwards towards the reservoir rather than to the detector. Thus, in order to ensure sufficient pressure and flow rate at the entrainment zone in a gravity driven system, large or pressurized reservoirs are required Furthermore, the reservoir would have to be kept at a constant level or pressure so that the pressure at the entrainment zone (and therefore the flow rate) would be constant. These limitations make gravity driven systems cumbersome. Consequently, a pumping system is preferred.

After the solvent entrains the effluent from the GC column 12, the resulting stream is carried from the entrainment zone by tubing 26 to a detector 24. Detector 24 can be any detector designed for the analysis of analytes in the liquid phase (e.g. electrochemical, fluorescence, or spectrometers such as ultraviolet detectors: for further examples see Douglas A. Skoog and Donald M. West, *Principles of Instrumental Analysis,* 1980). Detectors designed for liquid analysis typically contain a flow through cell 25, as shown in FIG. 1. This cell preferably has a volume of between 10 and 1000 $\mu l$, most preferably about 500 $\mu l$. The effluent from the detector 24 is typically directed to a waste collection device 28 via tubing 27, also shown in FIG. 1.

As should be clear from the foregoing description, the present invention provides a means for injecting a sample onto a gas chromatography column, separating the sample into its various components, trapping the components in a liquid stream and detecting the analytes with a detector designed for analyzing liquids, without seriously degrading the resolution achieved by the gas chromatography instrument.

Another objective of the present invention is to specifically provide a means for coupling the output from a capillary gas chromatography column to a liquid radioactivity monitor. Liquid radioactivity monitors require a scintillator to be mixed with a sample which emits ionizing radiation. The liquid radioactivity monitor then measures the level of scintillation which indicates the presence of analytes.

By mixing a scintillating material with the solvent in the reservoir 23, the apparatus described above can be used to effectively couple a capillary gas chromatograph with a liquid radioactivity monitor. The radioactivity monitor itself can be a Packard model 7150, but other commercially available liquid radioactivity monitors will suffice. Furthermore, the solvent chosen should be inert towards the scintillating material, and the scintillating material and the solvent should be miscible.

In some applications, gas bubbles from the gas used to carry the sample through the gas chromatography column may interfere with the detection system. Therefore, a degassing device such as a gas permeable membrane (e.g. an optimized version of LDC Analytical's membrane degasser, part number 920603001) can be inserted in line 26, after the entrainment zone 19 but before the detector. With a degassing device in place, the versatility of the invention is dramatically increased.

The present invention also lends itself to carrying out on-line liquid-phase derivatization reactions. Often, the detection of the analytes from a gas chromatographic instrument can be improved by first reacting the analytes with a fast reacting reagent. The reaction product, can then be detected by the detector. For example, species which are not readily detectable by a particular type of detector can be converted to a species which can be detected, or highly reactive species which might otherwise react with the surfaces in the detector can be neutralized. Many other examples of such types of applications are reported in the liquid chromatography and flow injection analysis literature (see e.g. Daniel Knapp, *Handbook of Analytical Derivatization Reactions*, John Wiley & Sons, Ino., 1979).

Before this invention, in order to derivatize and detect analytes from a gas chromatograph, it was usually the case that samples were taken at various intervals, removed from the stream of gaseous effluent, derivatized and analyzed. Consequently, as the procedure could not continually derivatize the effluent, only individual data points could be obtained. Consequently, the analyst was forced to extrapolate to estimate the values for the effluent between the points where a sample was taken.

In the present invention, the derivatizing reagent can be added to the reservoir 23, and then continuously pumped into the entrainment zone 19. Additionally, it may be necessary to add another mixing device after the entrainment zone 19 to ensure that the sample and derivatizing reagent are thoroughly mixed. Furthermore, it is important that the solvent chosen is inert towards the derivatizing agent and readily mixes with the derivatizing agent.

Accordingly, the pump 20 will continually add a derivatizing agent to the effluent from the gas chromatography column 12, and the additional mixing device will facilitate a quick reaction, ensuring that the analytes will be reacted by the time the sample reaches the detector. It should be appreciated that the interface of this invention allows the reagent to continually react with the analytes as they elute from the gas chromatography column. Thus, a continual spectrum of the derivatized sample can be obtained, eliminating the need for extrapolating between data points.

Figure 5:
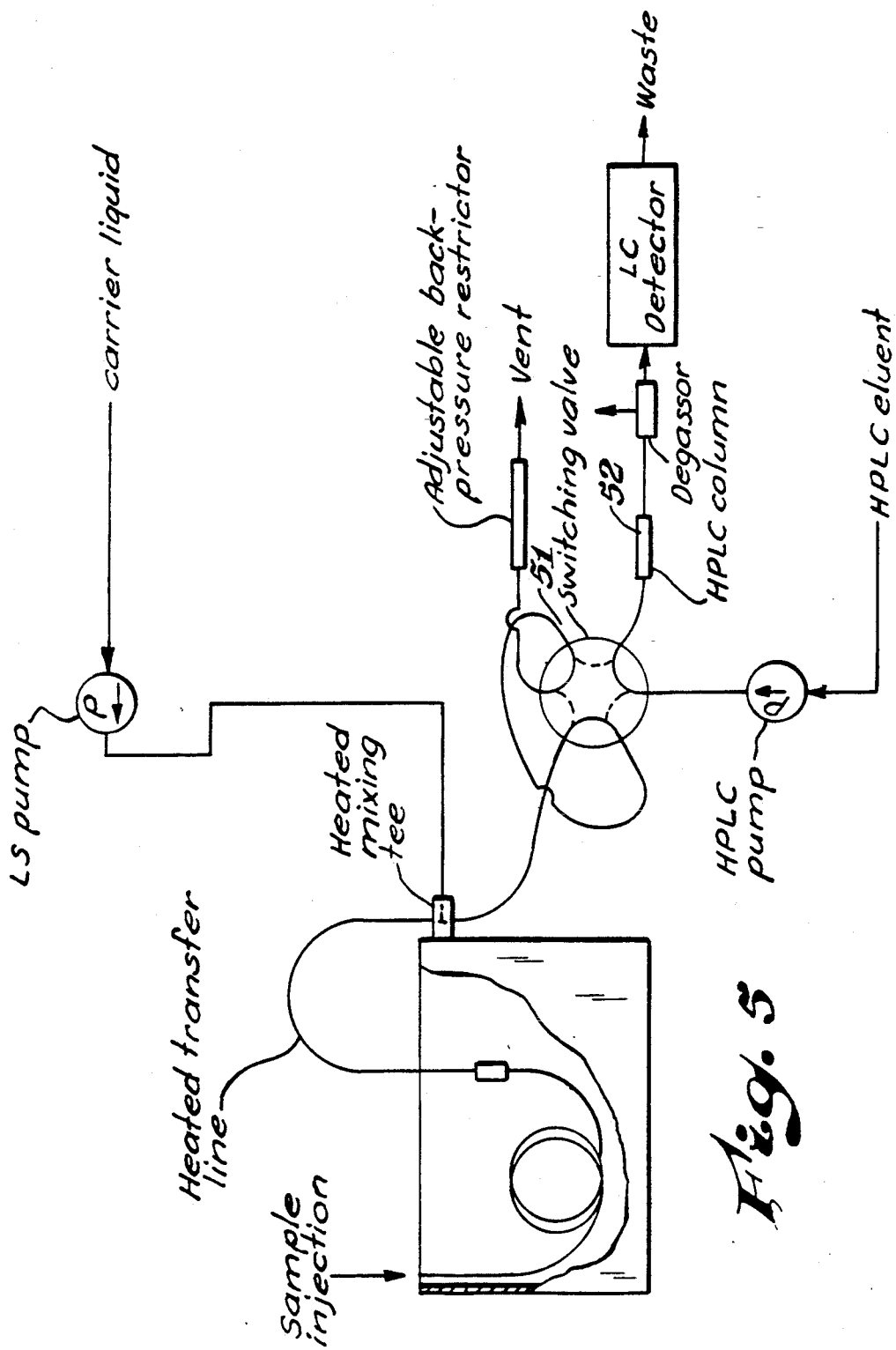
FIG. 5 is a schematic drawing of a multidimensional chromatography system which uses an interface, a heated transfer line and an entrainment zone arranged according to the principles of this invention.

Additionally, as seen in FIG. 5, multidimensional chromatography can be achieved using the interface of the present invention with a switching valve 51 containing a sample loop 52 placed immediately after the entrainment zone 19. The switching valve 51 and sample loop 52 act as an interface between the low pressure of the gas chromatograph and the high pressure of another type of chromatographic system. This configuration allows a gaseous sample to be eluted through a gas chromatography column, entrained by a suitable solvent at near ambient pressure and then routed into the sample loop of the switching valve. Once the sample is confined within the sample loop, the valve is switched, allowing pressurized solvent (e.g. 100–10,000 psig) from a high performance liquid chromatography (HPLC) or a supercritical fluid chromatography (SFC) system to carry the solvent to a second separation column 52. The interface allows the separation obtained by the gas chromatograph to be maintained while the material is transferred to the HPLC system. The effectiveness of the invention is demonstrated in the following example:

EXAMPLE

A stock solution of $^{14}$C-Benzene in acetone was assayed in triplicate. It was determined that the solution contained 244817 dpm/$\mu$L. This stock solution was then used to prepare standard solutions by diluting the amount of stock solution listed in Table I with acetone to form 1000 $\mu$L standard solutions having the indicated activity.

TABLE I

| Stock solution added ($\mu$L) | dpm/2 $\mu$L |
|---|---|
| 2 | 979 |
| 4 | 1959 |
| 8 | 3917 |
| 20 | 9793 |
| 100 | 48963 |
| 200 | 97927 |

Figure 6:
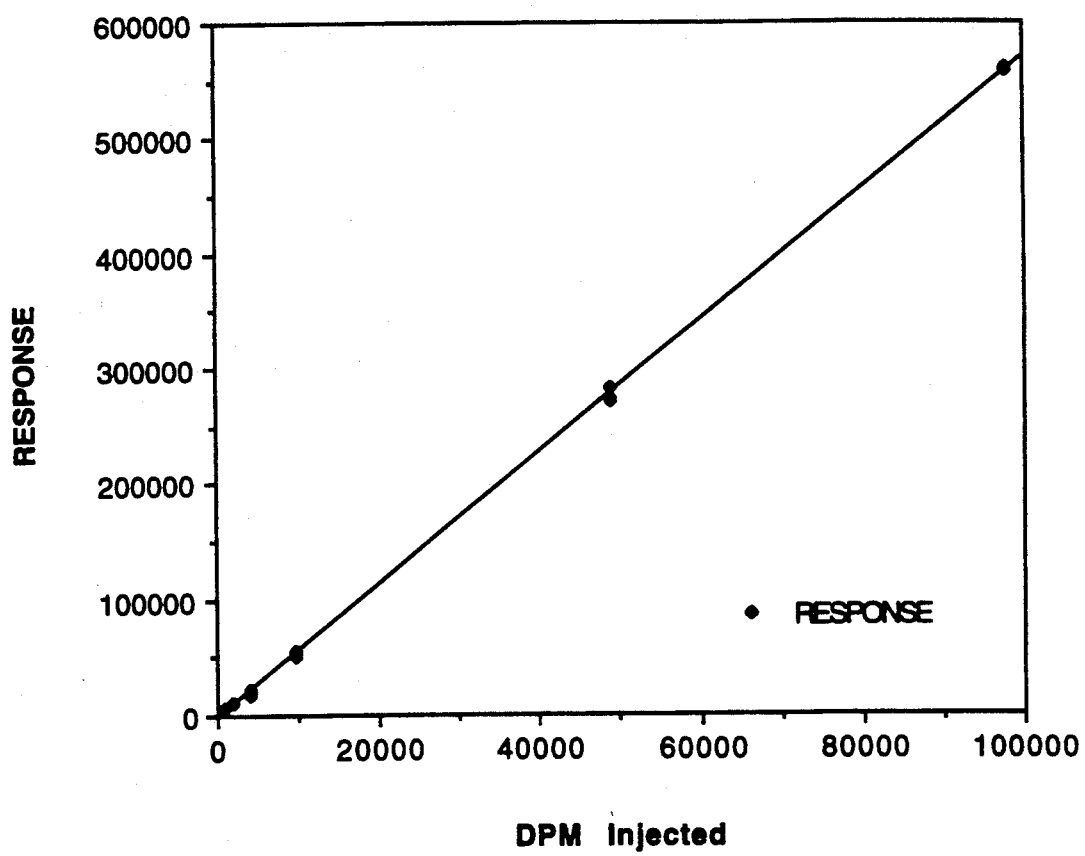
FIG. 6 is a graph demonstrating that an apparatus constructed according to the principles of the present invention provides a linear response according to the concentration of the analyte injected.

These standards were then analyzed in triplicate using the method and apparatus of the invention. The particular parameters used for the analysis are as follows:

Gas Chromatograph-
Hewlett Packard model HP5890
Carrier - He at 20 psi (oven at 40° C.)
Column - DB-624 30 w 1.8 $\mu$m
Injection Port - Direct at 250° C.
Injection size - 2 $\mu$L
Oven - 40° C. for 5 min, ramp at 15° C./min to 175° C., hold for 1 min
Transfer Line- 160° C.
Tee- 100° C.
Detector
Liquid Radioactivity Monitor
Pump - Waters M45
Eluant - 15/85 AQUASOL TM /Acetonitrile
Flow - 3 mL/min.
RAM- Packard Trace II
Mode - Homogeneous
Nuclide - $^{14}$C
Flow cell - 500 $\mu$L The detector response was plotted against the known activity levels. This plot appears as FIG. 6. As seen from this figure, the GC/LRAM system responded linearly according to the concentration of the standard analyzed.

Next the precision of the instrument was determined using two of the standard solutions described above. The standard containing 979 dpm/2 µL, and the standard containing 48963 dpm/2 µL were each injected seven times using the same parameters as described above. The injections of the standard containing 979 dpm/2 µL resulted in a relative standard deviation of 12%, and the injections of the standard containing 48963 dpm/2 µL provided a relative standard deviation of 2%.

Next, the sample recovery of the system was evaluated. For this evaluation the materials indicated in Table II were injected into the apparatus configured as described above. The waste collection device 28 was removed and the conduit 27 from the liquid detector was routed to glass collection vessels which were kept on dry ice to minimize vaporization of the effluent. The collection vessels were carefully weighed before and after collection and then assayed for radioactivity to allow calculation of recovery efficiency. The results are presented in Table II.

TABLE II

| Material | % recovery |
| --- | --- |
| $^{14}$C-trichloroethylene | 94.8 ± 1.1 |
| $^{14}$C-perchloroethylene | 97.2 ± 1.7 |
| $^{14}$C-dipropylene glycol dimethyl ether | 98.1 ± 1.3 |
| $^{14}$C-dipropylene glycol | 95.2 ± 1.8 |
| $^{14}$C-tripropylene glycol | 96.7 ± 5.7 |

Figure 7:
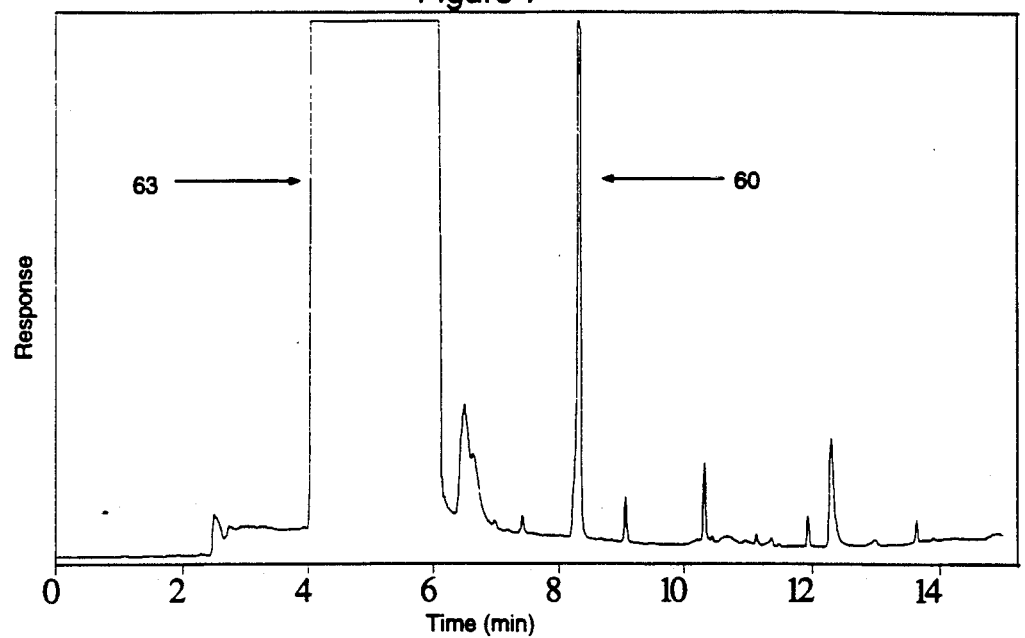
FIG. 7 is a copy of a chromatogram obtained from an FID detector of a sample injected into a gas chromatograph, separated using a capillary column and split to two different detectors, thereby allowing a direct comparison of the chromatograms produced by two detection systems on the identical sample injection.
Figure 8:
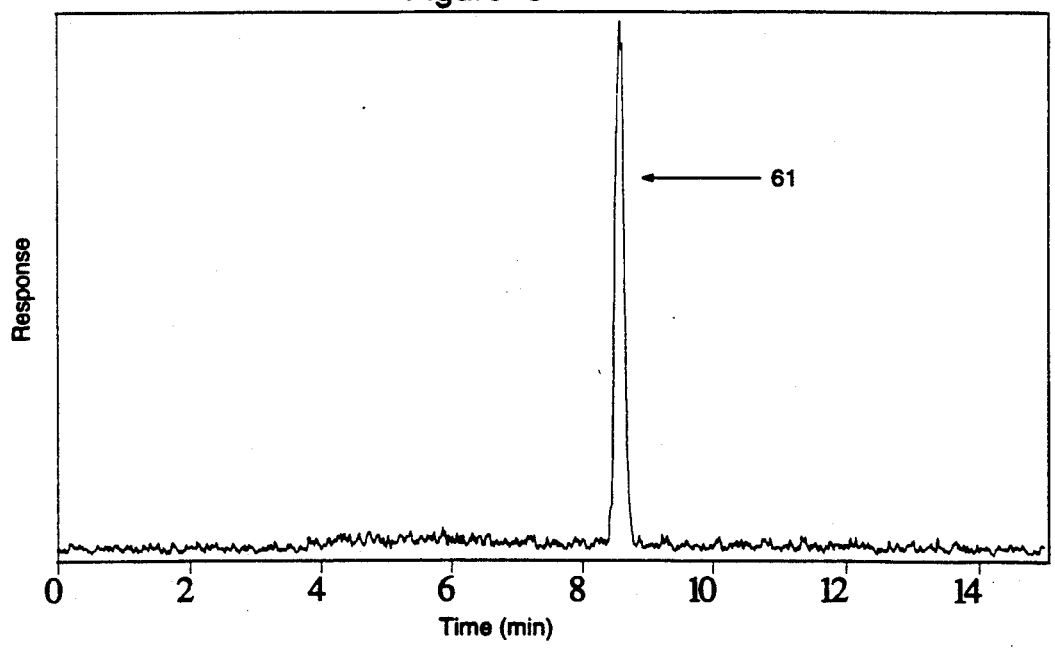
FIG. 8 is a copy of a chromatogram obtained using the method and apparatus of the present invention, resulting from the same injection and generated simultaneously with the chromatogram in FIG. 7.

Finally, an experiment was conducted to provide comparative data between the GC/LRAM system of the present invention and a GC/FID system typically used to analyze the effluent from a gas chromatography column. A "Y" splitter was inserted before the heated transfer line. One branch of the Y-splitter went to the liquid radioactivity monitor operating at the same parameters as above. The second branch of the Y-splitter was directed to a flame ionization detector (FID), labelled 13 in FIG. 1. Thus the same sample was analyzed by a detector designed for analyzing gases, and a detector designed for analyzing liquids. The FID response is seen in FIG. 7, while the LRAM response is seen in FIG. 8. Peak 60 in FIG. 7 and Peak 61 represent the $^{14}$C-benzene peak in the respective chromatograms. The extra peaks observed in the FID response correspond to acetone (peak 63) and impurities which were not labelled with radioactive isotopes. As can be seen from a comparison of FIGS. 7 and 8, the peak width of the $^{14}$C-benzene peak is nearly as narrow for the LRAM monitor as it is for the FID monitor. FIGS. 7 and 8 were enlarged and analyzed and it was determined that the GC/LRAM system demonstrated an apparent chromatographic efficiency of 30,000 theoretical plates, whereas the GC/FID system provided 190,000 theoretical plates.

The foregoing is provided for exemplary purposes only, and it is evident that those skilled in the art, once given the benefit of this disclosure, may make modifications of the specific embodiments described herein without departing from the spirit of the invention. Such modifications are to be considered within the scope of the present invention which is limited solely by the scope and spirit of the appended claims.

What is claimed is:

1. A method of detecting resolved, structurally distinct analytes in a gaseous effluent stream from a gas chromatography instrument, comprising the steps of:
    (a) forming a liquid-gas stream by entraining the gaseous effluent stream with a stream of liquid solvent such that the analytes retain their structural distinctiveness and generally retain the resolution achieved by the gas chromatography instrument;
    p1 (b) allowing at least a portion of the analytes to be transferred from the gaseous effluent stream to the liquid solvent stream;
    (c) conveying the liquid solvent stream containing analytes from the gaseous effluent stream to a detector designed for liquid analysis which is responsive to the presence of the analytes; and
    (d) detecting the distinct analytes.

2. The method of claim 1 wherein the gaseous effluent is maintained at a temperature sufficient to prevent the analytes resolved by the gas chromatography instrument from reuniting.

3. The method of claim 1 wherein the stream of liquid solvent is formed using a pumping means.

4. The method of claim 1 wherein step (a) includes directing the gaseous effluent stream to one arm of a tee and pumping the liquid solvent stream into another arm of a tee, such that the resulting liquid-gas stream flows out of a last arm of the tee.

5. The method of claim 1 wherein step (b) is facilitated by forming a segmented liquid-gas stream in step (a).

6. The method of claim 1 wherein the gas chromatography instrument includes a capillary column.

7. The method of claim 1 wherein the solvent contains a scintillating material and the detector is a liquid radioactivity monitor.

8. The method of claim 7 wherein the solvent is acetonitrile and the scintillating material is a liquid scintillation cocktail.

9. The method of claim 1 further comprising degassing the liquid-gas stream in between steps (b) and (c).

10. The method of claim 1 wherein the solvent contains a derivatizing agent effective for quickly reacting with the analytes forming a product which is more readily detected by the liquid chromatography detector.

11. The method of claim 1 further comprising the step of heating the region in which the liquid-gas stream is formed.

12. A chromatographic apparatus for separating and detecting structurally distinct analytes in a sample comprising:
    a gas chromatography instrument for separating a sample into structurally distinct analytes in a gaseous effluent stream;
    means for entraining the gaseous effluent stream from the gas chromatography instrument in a stream of liquid solvent such that the analytes retain their structural distinctiveness and the losses of resolution and chromatographic efficiency achieved by the chromatography instrument are minimized; and
    a detector capable of analyzing liquids in fluid communication with the means for entraining the gaseous effluent stream in a stream of liquid solvent.

13. The apparatus of claim 12 wherein the means for entraining the gaseous effluent stream from the gas chromatography instrument comprises:

a mixing means having a first and a second inlet ports and one outlet port;

a first conduit means connecting the exit line of the gas chromatography instrument with the first inlet of the mixing means;

a means for delivering the flow of a liquid solvent;

a second conduit means connecting the means for delivering the flow of a liquid solvent to the second inlet of the mixing means; and a third conduit means connecting the outlet port of the mixing means to the detector capable of analyzing liquids.

14. The apparatus of claim 13 further comprising a means for heating said first conduit means.

15. The apparatus of claim 13 wherein the means for delivering the flow of liquid solvent comprises a pump.

16. The apparatus of claim 13 further comprising a means for heating the mixing means.

17. The apparatus of claim 12 wherein the chromatography instrument comprises a capillary gas chromatograph.

18. The apparatus of claim 12 further comprising a degassing means located after the means for entraining the effluent and before the detector capable of analyzing liquids.

19. The apparatus of claim 12 wherein the detector capable of analyzing liquids is a liquid radioactivity monitor, and the liquid solvent contains a scintillating material.

20. An interface for coupling an output end of a gas chromatograph to a detector designed for liquid applications, comprising:

a low volume tee having two inlet ports and one outlet port;

a heated transfer means for connecting the output of the gas chromatograph directly to a first inlet port of the low volume tee;

a first conduit means for connecting a second inlet port of the low volume tee to a supply of solvent;

a second conduit means for connecting the output port of the low volume tee to a liquid chromatography detector.

21. The interface of claim 20 further comprising a means for heating the low volume tee.

* * * * *